US010577461B2

(12) United States Patent
Hwang et al.

(10) Patent No.: US 10,577,461 B2
(45) Date of Patent: Mar. 3, 2020

(54) POLYORGANOSILOXANE, AND COPOLYCARBONATE PREPARED BY USING THE SAME

(71) Applicant: LG CHEM, LTD., Seoul (KR)

(72) Inventors: Young Young Hwang, Daejeon (KR); Young Wook Son, Daejeon (KR); Moo Ho Hong, Daejeon (KR); Hyong Min Bahn, Daejeon (KR); Byoung Kue Chun, Daejeon (KR); Jung Jun Park, Daejeon (KR); Un Ko, Daejeon (KR); Ki Jae Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 141 days.

(21) Appl. No.: 15/742,000

(22) PCT Filed: Aug. 17, 2016

(86) PCT No.: PCT/KR2016/009044
§ 371 (c)(1),
(2) Date: Jan. 4, 2018

(87) PCT Pub. No.: WO2017/039190
PCT Pub. Date: Mar. 9, 2017

(65) Prior Publication Data
US 2018/0194894 A1 Jul. 12, 2018

(30) Foreign Application Priority Data

Sep. 4, 2015 (KR) .................. 10-2015-0125677

(51) Int. Cl.
| | | |
|---|---|---|
| *C08G 77/14* | (2006.01) | |
| *C08G 64/08* | (2006.01) | |
| *C07F 7/08* | (2006.01) | |
| *C08J 5/00* | (2006.01) | |
| *C08G 77/04* | (2006.01) | |
| *C08G 64/18* | (2006.01) | |
| *C08G 77/445* | (2006.01) | |
| *C08G 77/448* | (2006.01) | |
| *C08G 77/12* | (2006.01) | |
| *C08G 77/38* | (2006.01) | |
| *C08G 77/42* | (2006.01) | |
| *C08L 83/10* | (2006.01) | |
| *C08L 83/14* | (2006.01) | |

(52) U.S. Cl.
CPC .......... *C08G 64/085* (2013.01); *C07F 7/0838* (2013.01); *C08G 64/186* (2013.01); *C08G 77/04* (2013.01); *C08G 77/12* (2013.01); *C08G 77/38* (2013.01); *C08G 77/42* (2013.01); *C08G 77/445* (2013.01); *C08G 77/448* (2013.01); *C08J 5/00* (2013.01); *C08L 83/10* (2013.01); *C08L 83/14* (2013.01)

(58) Field of Classification Search
CPC .. C08G 64/085; C08G 64/186; C08G 77/448; C08G 77/14; C08G 77/46
See application file for complete search history.

(56) References Cited

U.S. PATENT DOCUMENTS

| | | | | |
|---|---|---|---|---|
| 3,203,926 | A * | 8/1965 | Deanin | C08G 64/06 528/204 |
| 5,112,925 | A | 5/1992 | Horlacher et al. | |
| 6,339,131 | B1 | 1/2002 | Cella et al. | |
| 6,762,250 | B2 | 7/2004 | Kanayama et al. | |
| 7,838,602 | B2 | 11/2010 | Davis et al. | |
| 8,802,804 | B2 * | 8/2014 | Kim | C08G 64/186 528/25 |
| 8,829,140 | B2 | 9/2014 | Huggins et al. | |
| 8,962,780 | B2 | 2/2015 | Higaki et al. | |
| 9,062,164 | B2 | 6/2015 | Kim et al. | |
| 9,434,840 | B2 | 9/2016 | Aoki | |
| 9,493,265 | B2 | 11/2016 | Stam et al. | |
| 9,718,958 | B2 * | 8/2017 | Son | C08G 64/24 |
| 9,732,186 | B2 * | 8/2017 | Bahn | C08G 64/186 |
| 10,294,365 | B2 * | 5/2019 | Lee | C08L 69/00 |
| 2014/0249280 | A1 * | 9/2014 | Kim | C08G 77/48 525/464 |
| 2016/0009859 | A1 * | 1/2016 | Marshall | C08G 65/40 528/207 |
| 2016/0122477 | A1 | 5/2016 | Rhee et al. | |

FOREIGN PATENT DOCUMENTS

| | | |
|---|---|---|
| EP | 0522752 A2 | 1/1993 |
| EP | 2857384 A1 | 4/2015 |
| JP | 11311870 A | 11/1999 |
| JP | 2004143412 A | 5/2004 |
| JP | 4223720 B2 | 2/2009 |
| JP | 2014513750 A | 6/2014 |
| JP | 2016-524646 A | 8/2016 |
| KR | 1020110108610 A | 10/2011 |

(Continued)

OTHER PUBLICATIONS

Vjacheslav V. Zuev, "The Catalytic Isomerization of Terminal Carbon-Carbon Double Bonds in Liquid Crystalline Polyesters at Hydrosilation with 1-(1'-Arylethoxy)-1,1,3,3-Tetramethyl Disiloxanes", Phosphorus, Sulfur, and Silicon and the Related Elements, 2006, vol. 181, No. 9, pp. 2063-2078.

*Primary Examiner* — Margaret G Moore
(74) *Attorney, Agent, or Firm* — Dentons US LLP

(57) ABSTRACT

Provided are a novel polyorganosiloxane capable of preparing copolycarbonate with improved weather resistance and flowability while maintaining the intrinsic physical properties of polycarbonate resin, and a copolycarbonate prepared by using the same.

14 Claims, 2 Drawing Sheets

(56) References Cited

FOREIGN PATENT DOCUMENTS

| | | |
|---|---|---|
| KR | 1020120050968 A | 5/2012 |
| KR | 1020130047612 A | 5/2013 |
| KR | 1020130111213 A | 10/2013 |
| KR | 1020140084858 A | 7/2014 |
| KR | 1020140116921 A | 10/2014 |
| KR | 1020160002485 A | 1/2016 |
| WO | 2012073970 A1 | 6/2012 |
| WO | 2013066002 A1 | 5/2013 |

* cited by examiner

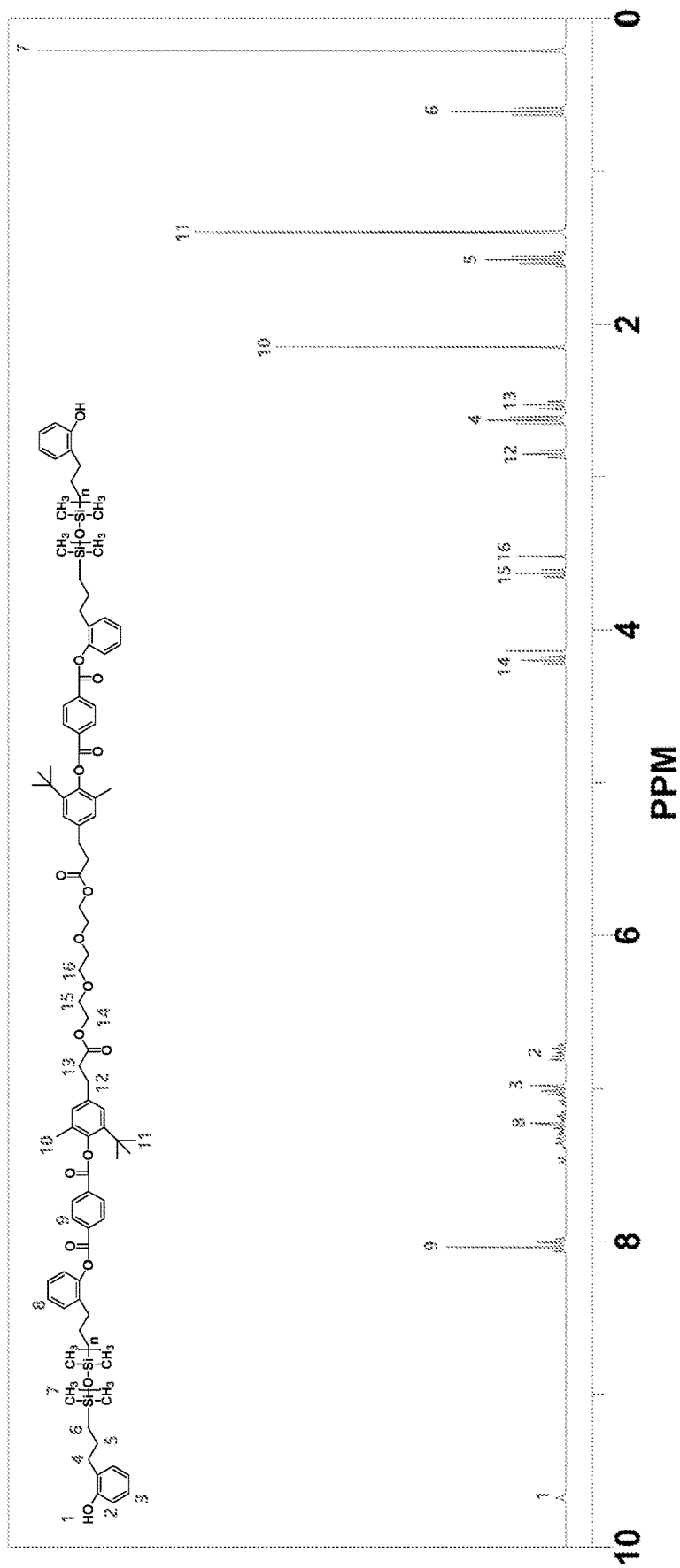
[Fig. 1]

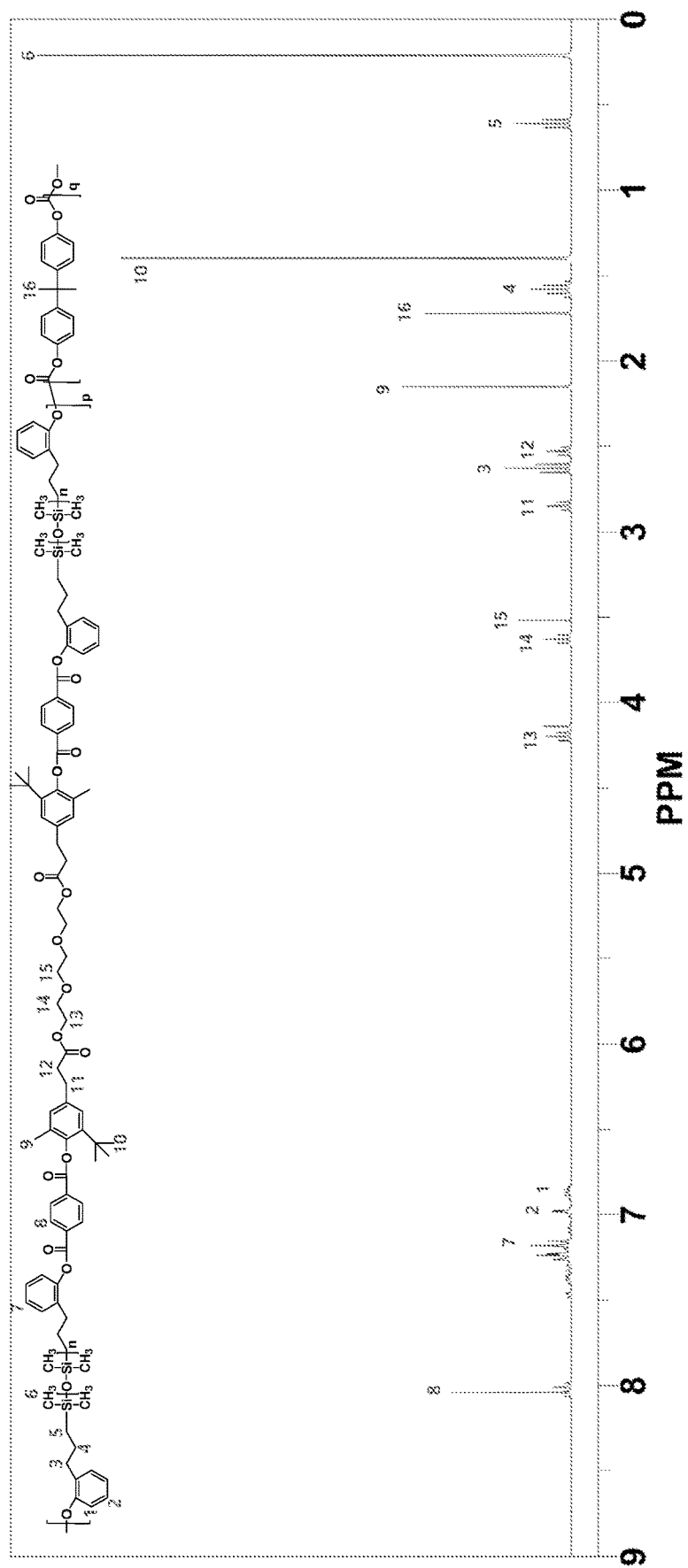
[Fig. 2]

POLYORGANOSILOXANE, AND COPOLYCARBONATE PREPARED BY USING THE SAME

CROSS REFERENCE TO RELATED APPLICATIONS

This application is a National Stage Application of International Application No. PCT/KR2016/009044, filed Aug. 17, 2016, and claims the benefit of Korean Patent Application No. 10-2015-0125677, filed Sep. 4, 2015, contents of which are incorporated herein by reference in their entirety for all purposes as if fully set forth below.

TECHNICAL FIELD

The present invention relates to a novel polyorganosiloxane capable of preparing copolycarbonate with improved weather resistance and flowability, and a copolycarbonate prepared by using the same.

BACKGROUND OF ART

Polyorganosiloxane as a kind of silicone means a polymer having a siloxane bond substituted with organic groups as a main chain. For example, polyorganosiloxane is prepared by condensation polymerization of an aromatic diol such as bisphenol A and a carbonate precursor such as phosgene, and is colorless, odorless, resistant to oxidation, and stable at room temperature, and hypoallergenic insulators, and used in electrics, electronics, vehicles, machines, medicine, cosmetics, lubricants, adhesives, gaskets, artificial aids for plastic surgery or the like.

In addition, polyorganosiloxane has superior impact strength, dimensional stability, heat-resistance, transparency or the like, and is applied to a variety of fields such as exterior materials of electrical and electronic products, vehicle components, construction materials, optical components or the like. Recently, many studies have been conducted to apply the copolycarbonate resin to a wider variety of fields, in which two or more aromatic diols having different structures are copolymerized to introduce a monomer having a different structure to a main chain of polycarbonate, thereby obtaining desired properties.

Particularly, researches to introduce a polysiloxane structure to a main chain of polycarbonate are also being performed. However, most technologies have disadvantages that production costs are high and chemical resistance and impact strength are not improved at the same time.

However, with expansion of the application fields of copolycarbonate, copolycarbonate are required to have higher weather resistance and flowability, and accordingly, there is a demand for a novel structure of copolycarbonate which is able to improve weather resistance and flowability while maintaining its intrinsic physical properties.

BRIEF DESCRIPTION OF THE DRAWINGS

FIG. 1 is the $^1$H NMR graph of the polyorganosiloxane prepared in Example 1 of this application.

FIG. 2 is the $^1$H NMR graph of the copolycarbonate resin prepared in Example 1 of this application.

DETAILED DESCRIPTION OF THE INVENTION

[Technical Problem]
The present invention provides a novel polyorganosiloxane capable of preparing copolycarbonate with improved weather resistance and flowability.

Further, the present invention provides a copolycarbonate prepared by using the polyorganosiloxane.

Furthermore, the present invention provides a molded article manufactured by using the copolycarbonate.

[Technical Solution]
The present invention provides a polyorganosiloxane represented by the following Chemical Formula 1.

Further, the present invention provides a copolycarbonate having a weight average molecular weight of 1,000 to 100,000 g/mol, which includes a repeating unit represented by the following Chemical Formula 2 and a repeating unit represented by the following Chemical Formula 3.

Furthermore, the present invention provides a molded article manufactured by using the copolycarbonate.

Hereinafter, a polyorganosiloxane, a copolycarbonate, and a molded article according to specific embodiments of the present invention will be described in more detail.

According to an embodiment of the present invention, provided is a polyorganosiloxane represented by the following Chemical Formula 1:

B-A-B     [Chemical Formula 1]

wherein A is

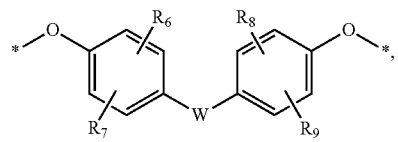

B is

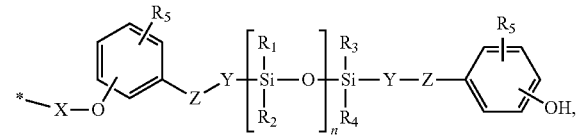

$R_1$ to $R_4$ are each independently hydrogen or $C_{1-10}$ alkyl,
$R_5$ is hydrogen, halogen, hydroxy, $C_{1-10}$ alkyl, $C_{1-10}$ alkoxy, or $C_{6-10}$ aryl,
$R_6$ to $R_9$ are each independently hydrogen, $C_{1-10}$ alkyl, or halogen,
X is —CO— or —CO—($C_{6-10}$ arylene)-CO—,
Y is $C_{1-10}$ alkylene,
Z is a bond, —OCO— or —COO—,
W is a divalent functional group containing —($C_{1-10}$ alkylene)-O—, and
n is an integer of 1 to 99.

Polyorganosiloxane as a kind of silicone means a polymer having a siloxane bond substituted with organic groups as a main chain. Of polyorganosiloxanes, particularly, the polyorganosiloxane represented by Chemical Formula 1 of an embodiment may exhibit all of the effect by a silicone monomer and the effect of a linker represented by A of Chemical Formula 1 and an ester structure. Therefore, the polyorganosiloxane is characterized in that it has improved weather resistance due to the Fries rearrangement effect and improved flowability due to improvement of internal chain mobility of the ester structure and the ether structure while maintaining high ductility.

Further, W in Chemical Formula 1 is preferably a divalent functional group containing —($C_{1-10}$ alkylene)—COO—($C_{1-10}$ alkylene)-O—.

Further, A is more preferably

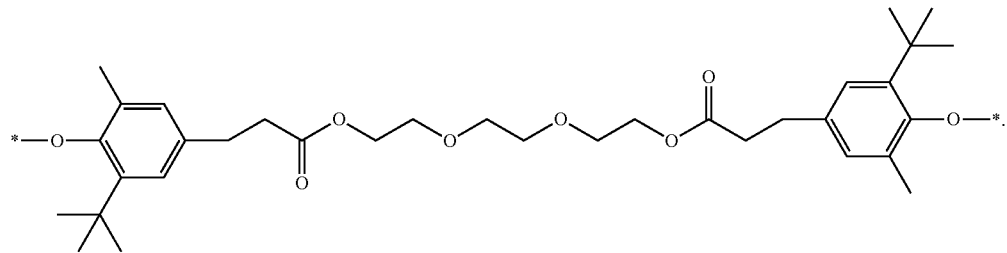

Further, in Chemical Formula 1, $R_1$ to $R_4$ are preferably each independently hydrogen or $C_{1-4}$ alkyl.

Further, $R_5$ is preferably hydrogen or $C_{1-4}$ alkoxy.

Further, $R_6$ to $R_9$ are preferably each independently hydrogen or $C_{1-4}$ alkyl.

Further, X is preferably —CO-(phenylene)-CO—.

Further, Y is preferably $C_{1-5}$ alkylene.

Further, a specific example of the polyorganosiloxane represented by Chemical Formula 1 may be the following compound:

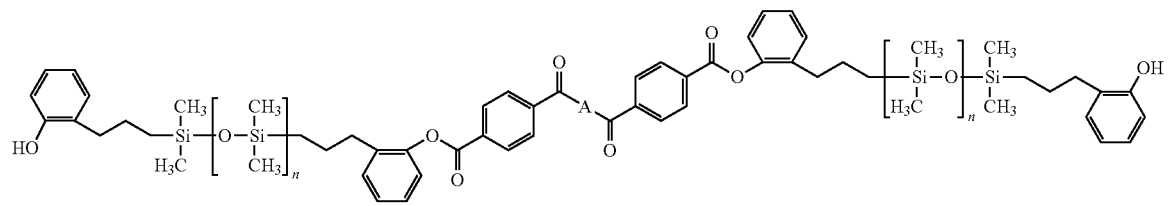

wherein A is

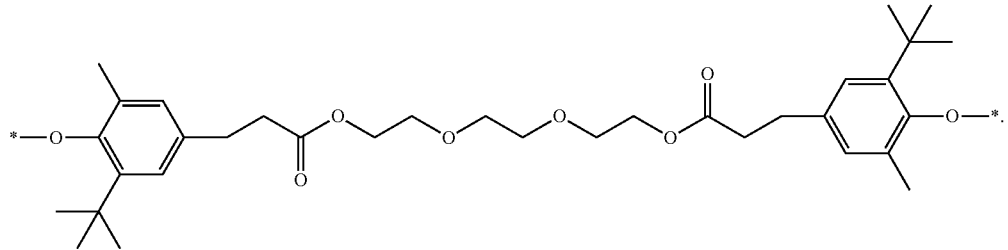

Meanwhile, the polyorganosiloxane of an embodiment may be synthesized by a method as in the following Reaction Scheme 1, but is not limited thereto, and a method of preparing the compound represented by Chemical Formula 1 will be described in more detail in Examples described below:

[Reaction Scheme 1]

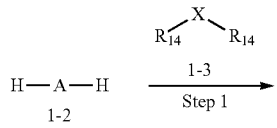

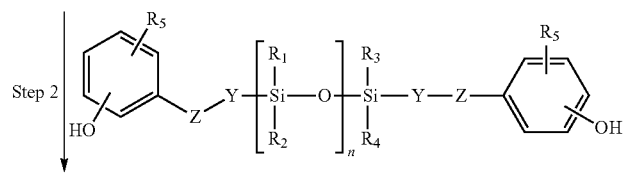

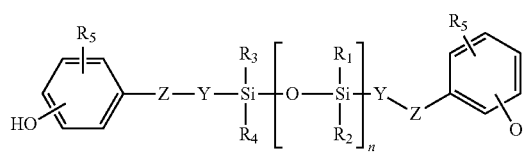

wherein $R_1$ to $R_5$, X, Y, Z, and n are the same as defined in Chemical Formula 1, and $R_{14}$ is hydroxy or halogen, preferably hydroxy or chloro.

Step 1 is a step of preparing a compound represented by Chemical Formula 1-4 by reacting a compound represented by Chemical Formula 1-2 with a compound represented by Chemical Formula 1-3 which is a carbonate-based compound. In this regard, a molar ratio of the compound represented by Chemical Formula 1-2 and the compound represented by Chemical Formula 1-3 is preferably 1:1.1 to 1:5, and more preferably 1:1.3 to 1:2.5, and in the reaction, chloroform is preferably used as a solvent. Further, the reaction is preferably performed at room temperature.

Step 2 is a step of preparing the compound represented by Chemical Formula 1 by reacting the compound represented by Chemical Formula 1-4 with a compound represented by Chemical Formula 1-5 which is a polysiloxane compound. A molar ratio of the compound represented by Chemical Formula 1-4 and the compound represented by Chemical Formula 1-5 is preferably 1:1.1 to 1:5, and more preferably 1:1.3 to 1:2.5, and in the reaction, chloroform is preferably used as a solvent. Further, the reaction is preferably performed at room temperature.

According to another embodiment of the present invention, provided is a copolycarbonate having a weight average molecular weight of 1,000 to 100,000 g/mol, which includes a repeating unit represented by the following Chemical Formula 2 and a repeating unit represented by the following Chemical Formula 3:

wherein A is

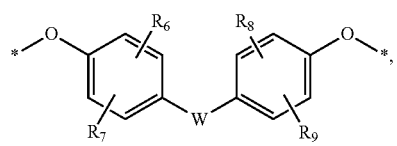

$R_1$ to $R_4$ are each independently hydrogen or $C_{1-10}$ alkyl,
$R_5$ is hydrogen, halogen, hydroxy, $C_{1-10}$ alkyl, $C_{1-10}$ alkoxy, or $C_{6-10}$ aryl,
$R_6$ to $R_9$ are each independently hydrogen, $C_{1-10}$ alkyl, or halogen,
X is —CO— or —CO—($C_{6-10}$ arylene)-CO—,
Y is $C_{1-10}$ alkylene,
Z is a bond, —OCO— or —COO—,
W is a divalent functional group containing —($C_{1-10}$ alkylene)-O—, and
n is an integer of 1 to 99,

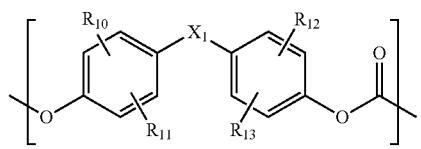

wherein $X_1$ is $C_{1-10}$ alkylene unsubstituted or substituted with phenyl, $C_{3-6}$ cycloalkylene, O, S, SO, $SO_2$, or CO, and $R_{10}$ to $R_{13}$ are each independently hydrogen, $C_{1-10}$ alkyl, or halogen.

In Chemical Formula 2, A, $R_1$ to $R_9$, X, Y, Z, and n are the same as those described in Chemical Formula 1 without limitation.

$X_1$ is preferably $C_{1-4}$ alkylene unsubstituted or substituted with phenyl, $C_{3-6}$ cycloalkylene, O, S, SO, $SO_2$ or CO.

[Chemical Formula 2]

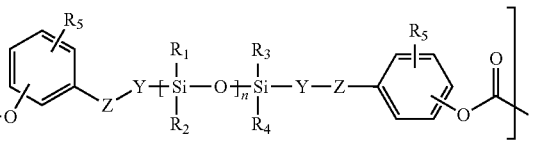

Further, $R_{10}$ to $R_{13}$ are preferably each independently hydrogen, $C_{1-4}$ alkyl, chloro, or bromo.

The copolycarbonate of an embodiment may be prepared by polymerizing the polyorganosiloxane represented by Chemical Formula 1, an aromatic diol compound, and a carbonate precursor, and as described above, the copolycarbonate is characterized in that it has improved weather resistance and flowability while maintaining ductility of copolycarbonate due to improvement of internal mobility by the ester or ether structure in the polyorganosiloxane represented by Chemical Formula 1.

The aromatic diol compound is a compound represented by the following Chemical Formula 4, and corresponds to Chemical Formula 3:

[Chemical Formula 4]

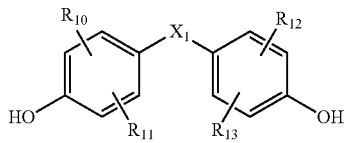

wherein $X_1$ and $R_{10}$ to $R_{13}$ are the same as defined in Chemical Formula 3.

Specific examples of the aromatic diol compound may include bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulphide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane(bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, or 1,1-bis(4-hydroxyphenyl)-1-phenylethane.

The carbonate precursor functions to link the compound represented by Chemical Formula 1 with the compound represented by Chemical Formula 4, and specific examples thereof may include phosgene, triphosgene, diphosgene, bromophosgene, dimethyl carbonate, diethyl carbonate, dibutyl carbonate, dicyclohexyl carbonate, diphenyl carbonate, ditolyl carbonate, bis(chlorophenyl) carbonate, m-cresyl carbonate, dinaphthyl carbonate, bis(diphenyl) carbonate, or bishaloformate.

Further, the copolycarbonate of an embodiment may be prepared by including the step of polymerizing a composition including the polyorganosiloxane represented by Chemical Formula 1, the aromatic diol compound, and the carbonate precursor.

Upon the polymerization, the polyorganosiloxane represented by Chemical Formula 1 may be used in an amount of 0.1% by weight or more, 1% by weight or more, or 3% by weight or more, and 20% by weight or less, 10% by weight or less, or 7% by weight or less, based on 100% by weight of the composition.

Further, the aromatic diol compound may be used in an amount of 40% by weight or more, 50% by weight or more, or 55% by weight or more, and 80% by weight or less, 70% by weight or less, or 65% by weight, based on 100% by weight of the composition.

Further, the carbonate precursor may be used in an amount of 10% by weight or more, 20% by weight or more, or 30% by weight, and 60% by weight or less, 50% by weight or less, or 40% by weight or less, based on 100% by weight of the composition.

In this regard, the polymerization may be preferably performed by interfacial polymerization. Upon interfacial polymerization, the polymerization reaction is possible at low temperature under normal pressure, and it is easy to control the molecular weight.

The polymerization temperature is preferably 0° C. to 40° C., and the reaction time is preferably 10 minutes to 5 hours. Further, pH is preferably maintained at 9 or higher or at 11 or higher during reaction.

The solvent usable in the polymerization is not particularly limited, as long as it is a solvent usually used in the polymerization of copolycarbonate in the art, and for example, halogenated hydrocarbons such as methylene chloride, chlorobenzene, etc.

Further, the polymerization is preferably performed in the presence of an acid binder, and the acid binder may be alkali metal hydroxides such as sodium hydroxide, potassium hydroxide, etc., or an amine compound such as pyridine, etc.

Further, the polymerization is preferably performed in the presence of a molecular weight controller in order to control the molecular weight of copolycarbonate upon polymerization. As the molecular weight controller, $C_{1-20}$ alkylphenol may be used. Specific examples thereof may include p-tert-butylphenol, p-cumylphenol, decylphenol, dodecylphenol, tetradecylphenol, hexadecylphenol, octadecylphenol, eicosylphenol, docosylphenol, or triacontylphenol. The molecular weight controller may be injected before initiation of the polymerization, during initiation of the polymerization, or after initiation of the polymerization. The molecular weight controller may be, for example, included in an amount of 0.01 part by weight or more, 0.1 part by weight or more, or 1 part by weight or more, and 10 parts by weight or less, 6 parts by weight or less, or 5 parts by weight or less, based on 100 parts by weight of the aromatic diol compound. Within this range, a desired molecular weight may be obtained.

To promote the polymerization reaction, a reaction promoter, for example, a tertiary amine compound such as triethylamine, tetra-n-butylammoniumbromide tetra-n-butylphosphoniumbromide, etc., a quaternary ammonium compound, a quaternary phosphonium compound may be further used.

Further, the present invention provides a molded article manufactured by using the copolycarbonate. As describe above, flowability is improved while maintaining ductility of the copolycarbonate due to the structure derived from polypropylene glycol in the polyorganosiloxane represented by Chemical Formula 1, and therefore, the molded article may be applied to a variety of fields, compared to molded articles manufactured by using the previous copolycarbonate.

The molded article may further include, if necessary, one or more selected from the group consisting of an antioxidant, a plasticizer, an antistatic agent, a nucleating agent, a flame retardant, a lubricant, an impact modifier, an optical brightener, an ultraviolet absorber, a pigment, and a dye, in addition to the copolycarbonate according to the present invention.

A method of manufacturing the molded article may include, for example, the steps of mixing the copolycarbonate of the present invention and other additive using a mixer, extrusion-molding the mixture with an extruder to prepare a pellet, drying the pellet, and then injecting the pellet with an injection molding machine.

[Advantageous Effects]

A novel polyorganosiloxane according to the present invention may be used as a monomer of copolycarbonate, and it may have improved weather resistance and flowability while maintaining intrinsic physical properties of copolycarbonate, such as ductility.

[Detailed Description Of The Embodiments]

The present invention will be described in more detail with reference to the following Examples. However, the following Examples are for illustrative purposes only, and the disclosure of the present invention is not intended to be limited by the following Examples.

EXAMPLE 1

(Step 1) Preparation of Polyorganosiloxane

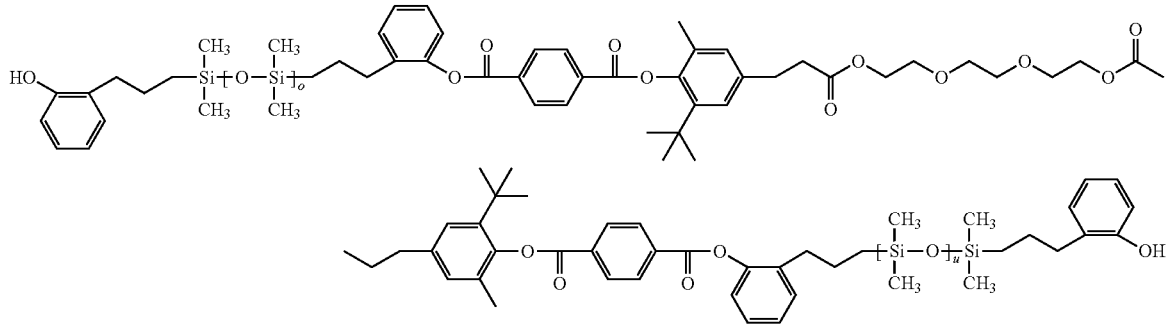

To a 2,000 mL-three neck reflux flask, 1,000 mL (liquid-based) of chloroform ($CHCl_3$) was added, 11.7 g of Anti-oxidant-245 (Ethylenebis(oxyethylene)bis[3-(5-tert-butyl-4-hydroxy-m-tolyl)propionate], Mw: 586 g/mol) and 7.1 g of terephthaloyl chloride were slowly dissolved at room temperature for 1 hour under a nitrogen atmosphere. Then, 25 of triethylamine was injected, and allowed to react for 1 hour, and 210 g of allylphenol polydimethylsiloxane (n: 43, Mw: 3,500 g/mol) was injected and sufficiently reacted to prepare a compound represented by the above Chemical Formula, and $^1H$ NMR graph thereof is shown in FIG. 1.

(Step 2) Preparation of Copolycarbonate Resin

To a polymerization reactor, 232 g of bisphenol A, 1,784 g of distilled water, and 385 g of sodium hydroxide were added, and mixed under a nitrogen atmosphere to completely dissolve bisphenol A. Then, 875 g of methylene chloride, 4.3 g of PTBP (para-tert butylphenol) and 7.0 g of the compound prepared in Step 1 (solid-based, 5.2% by weight of polycarbonate resin) were injected and mixed. 130 g of TPG (triphosgene) dissolved in 920 g of methylene chloride was added dropwise thereto for 1 hour, and at this time, pH was maintained at 11 using a sodium hydroxide aqueous solution. After completion of adding dropwise, the solution was aged for 15 minutes, and 46 g of triethylamine dissolved in methylene chloride was injected thereto. After a total reaction time of 1 hour and 30 minutes, pH was decreased to 4, and washing was performed using distilled water three times to separate a methylene chloride phase. A polymer thus obtained was precipitated in methanol, and dried at 120° C. to obtain a final powdery copolycarbonate resin. $^1H$ NMR graph thereof is shown in FIG. 2.

EXAMPLE 2

A copolycarbonate resin was prepared in the same manner as in Example 1, except that 120 g of allylphenol polydimethylsiloxane (n: 22, Mw: 2,000 g/mol) was used instead of allylphenol polydimethylsiloxane (n: 43, Mw: 3,500 g/mol).

EXAMPLE 3

A copolycarbonate resin was prepared in the same manner as in Example 1, except that in Step 2, 3.5 g (solid-based, 2.6% by weight of polycarbonate resin) of the compound prepared in Step 1 was used instead of 7.0 g thereof.

COMPARATIVE EXAMPLE 1

A copolycarbonate resin was prepared in the same manner as in Example 1, except that in Step 2, the compound prepared in Step 1 was not used.

EXPERIMENTAL EXAMPLE: EVALUATION OF PHYSICAL PROPERTIES OF COPOLYCARBONATE RESIN

The copolycarbonate resins obtained in Examples 1 to 3 and Comparative Example 1 were pelletized to prepare samples for evaluation of physical properties, and the physical properties of the samples were measured by the following method. The results are given in the following Table 1.

(1) Flowability (MFR, g/10 min): measured using the samples according to the standard ASTM D1238 (under conditions of 300° C. and 1.2 kg)

(2) Room temperature and low temperature impact strength (Notched Izod, J/m): measured according to ASTM D256(⅛ inch, Notched Izod) at 23° C. and −30° C., respectively.

(3) Weather resistance (ΔYI, 500 hrs): a yellow index difference (ΔYI) of the sample was measured for 500 hours using a QUV-A Accelerated Weathering Tester (Q-LAB) according to ASTM D4329.

(4) Weight average molecular weight (Mw, g/mol): measured by weighing with PC standard using Agilent 12000 series GPC.

TABLE 1

| Section | Example 1 | Example 2 | Example 3 | Comparative Example 1 |
|---|---|---|---|---|
| Flowability (g/10 min) | 9 | 15 | 11 | 10 |
| Room temperature impact strength (23° C., J/m) | 790 | 730 | 830 | 920 |
| Low temperature impact strength (−30° C., J/m) | 670 | 530 | 190 | 160 |
| Weather resistance (ΔYI) | 11 | 16 | 19 | 24 |
| Weight average molecular weight (g/mol) | 31,800 | 30,700 | 29,400 | 29,000 |

As shown in Table 1, the copolycarbonate resins prepared in Examples were found to have flowability and room temperature impact strength equivalent to or higher than those of Comparative Example 1 while having very excellent low temperature impact strength at −30° C. and weather resistance.

The copolycarbonate resins of Examples have superior low temperature impact strength and weather resistance which is a property of withstanding various weathers while maintaining the intrinsic physical properties of polycarbonate resin, thereby being easily applied to various fields such as exterior materials of electrical and electronic products, vehicle components, and construction materials.

The invention claimed is:

1. A polyorganosiloxane represented by the following Chemical Formula 1:

B-A-B    [Chemical Formula 1]

wherein A is

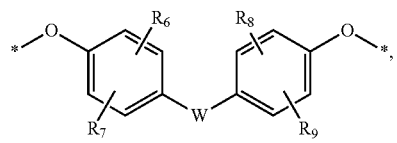

B is

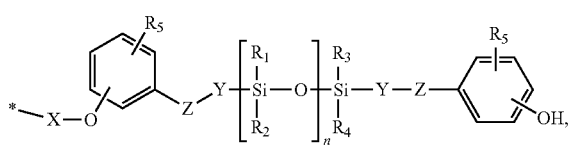

$R_1$ to $R_4$ are each independently hydrogen or $C_{1-10}$ alkyl,
$R_5$ is hydrogen, halogen, hydroxy, $C_{1-10}$ alkyl, $C_{1-10}$ alkoxy, or $C_{6-10}$ aryl,
$R_6$ to $R_9$ are each independently hydrogen, $C_{1-10}$ alkyl, or halogen,
X is —CO— or —CO—($C_{6-10}$ arylene)-CO—,
Y is $C_{1-10}$ alkylene,
Z is a bond, —OCO—, or —COO—,
W is a divalent functional group comprising —($C_{1-10}$ alkylene)-O—, and
n is an integer of 1 to 99.

2. The polyorganosiloxane of claim 1, wherein W is a divalent functional group comprising —($C_{1-10}$ alkylene)-COO—($C_{1-10}$ alkylene)-O—.

3. The polyorganosiloxane of claim 1, wherein A is

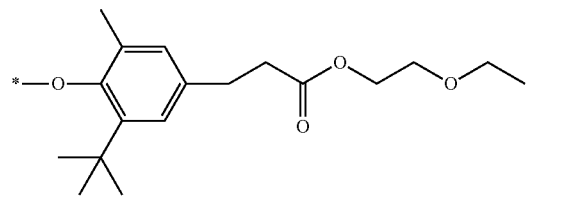

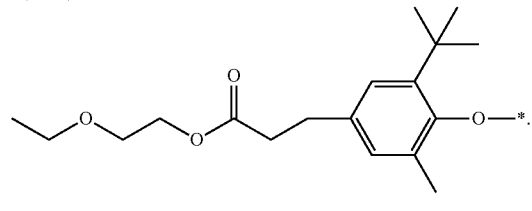

4. The polyorganosiloxane of claim 1, wherein $R_1$ to $R_4$ are each independently hydrogen or $C_{1-4}$ alkyl.

5. The polyorganosiloxane of claim 1, wherein $R_5$ is hydrogen or $C_{1-4}$ alkoxy.

6. The polyorganosiloxane of claim 1, wherein X is —CO-(phenylene)-CO—.

7. The polyorganosiloxane of claim 1, wherein Y is $C_{1-5}$ alkylene.

8. The polyorganosiloxane of claim 1, wherein the polyorganosiloxane has the following structure:

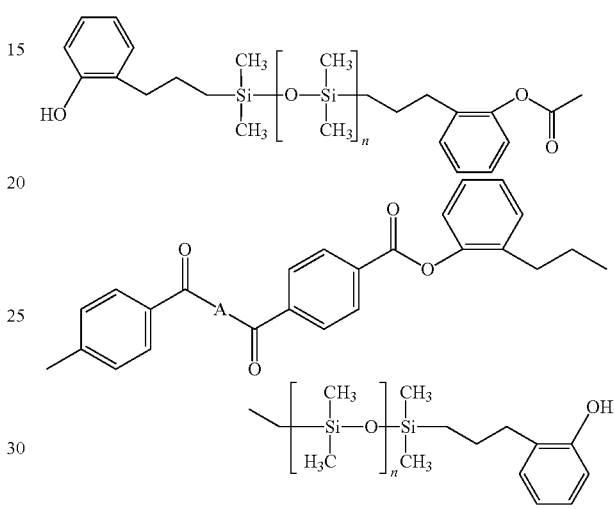

wherein A is

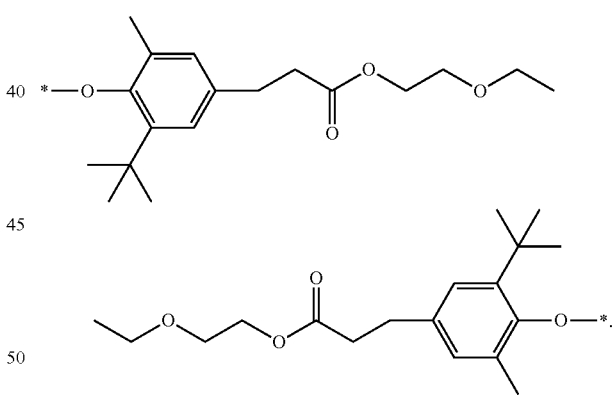

9. A copolycarbonate having a weight average molecular weight of 1,000 to 100,000 g/mol, which comprises a repeating unit represented by the following Chemical Formula 2 and a repeating unit represented by the following Chemical Formula 3:

[Chemical Formula 2]

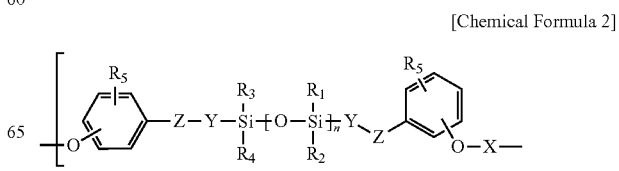

-continued

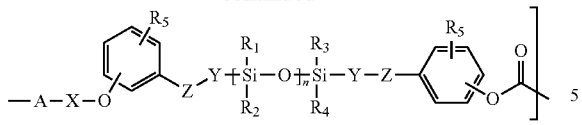

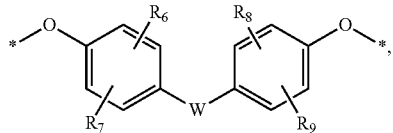

wherein A is $R_1$ to $R_4$ are each independently hydrogen or $C_{1-10}$ alkyl, $R_5$ is hydrogen, halogen, hydroxy, $C_{1-10}$ alkyl, $C_{1-10}$ alkoxy, or $C_{6-10}$ aryl, $R_6$ to $R_9$ are each independently hydrogen, $C_{1-10}$ alkyl, or halogen, X is —CO— or —CO—($C_{6-10}$ arylene)-CO—, Y is $C_{1-10}$ alkylene, Z is a bond, —OCO—, or —COO—, W is a divalent functional group comprising —($C_{1-10}$ alkylene)-O—, and n is an integer of 1 to 99,

[Chemical Formula 3]

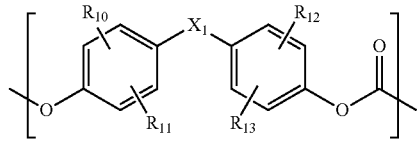

wherein $X_1$ is $C_{1-10}$ alkylene unsubstituted or substituted with phenyl, $C_{3-6}$ cycloalkylene, O, S, SO, $SO_2$, or CO, and $R_{10}$ to $R_{13}$ are each independently hydrogen, $C_{1-10}$ alkyl, or halogen.

10. The copolycarbonate of claim 9, wherein $X_1$ is $C_{1-4}$ alkylene unsubstituted or substituted with phenyl, $C_{3-6}$ cycloalkylene, O, S, SO, $SO_2$ or CO.

11. The copolycarbonate of claim 9, wherein $R_{10}$ to $R_{13}$ are each independently hydrogen, $C_{1-4}$ alkyl, chloro, or bromo.

12. A molded article manufactured by using the copolycarbonate of claim 9.

13. A molded article manufactured by using the copolycarbonate of claim 10.

14. A molded article manufactured by using the copolycarbonate of claim 11.

* * * * *